US011026745B2

(12) United States Patent
Guler et al.

(10) Patent No.: US 11,026,745 B2
(45) Date of Patent: Jun. 8, 2021

(54) OPEN-IRRIGATED ABLATION CATHETER WITH PROXIMAL INSERT COOLING

(71) Applicant: Boston Scientific Scimed inc., Maple Grove, MN (US)

(72) Inventors: Ismail Guler, Maple Grove, MN (US); Darrell L. Rankin, Milpitas, CA (US); David M. Flynn, Lino Lakes, MN (US); Robbie Halvorson, Plymouth, MN (US); Mark D. Mirigian, Houston, TX (US)

(73) Assignee: Boston Scientific Scimed Inc, Maple Grove, MN (US)

( * ) Notice: Subject to any disclaimer, the term of this patent is extended or adjusted under 35 U.S.C. 154(b) by 711 days.

(21) Appl. No.: 15/846,187

(22) Filed: Dec. 18, 2017

(65) Prior Publication Data

US 2018/0168724 A1   Jun. 21, 2018

Related U.S. Application Data

(60) Provisional application No. 62/436,398, filed on Dec. 19, 2016.

(51) Int. Cl.
  *A61B 18/14* (2006.01)
  *A61B 5/00* (2006.01)
  (Continued)

(52) U.S. Cl.
  CPC ........ *A61B 18/1492* (2013.01); *A61B 5/6852* (2013.01); *A61B 2017/00053* (2013.01);
  (Continued)

(58) Field of Classification Search
  CPC .... A61B 2018/0231; A61B 2018/1492; A61B 18/0218; A61B 18/1492; A61B 18/0231;
  (Continued)

(56) References Cited

U.S. PATENT DOCUMENTS 4,636,313 A   1/1987 Vaillancourt
5,413,107 A   5/1995 Oakley et al.
(Continued)

FOREIGN PATENT DOCUMENTS

CN   102232869 A   11/2011
CN   102232870 A   11/2011
(Continued)

OTHER PUBLICATIONS

International Preliminary Report on Patentability issued in PCT/US2013/073461, dated Jun. 18, 2015, 11 pages.
(Continued)

*Primary Examiner* — Michael F Peffley
*Assistant Examiner* — Bo Ouyang
(74) *Attorney, Agent, or Firm* — Faegre Drinker Biddle & Reath LLP

(57) ABSTRACT

An open-irrigated ablation catheter system includes a catheter body, and an electrode tip body mounted on a distal portion of the catheter body. The electrode tip body includes a proximal end configured for connection to the catheter body and a wall defining an open interior region and including one or more irrigation ports. The wall is conductive for delivering radio frequency (RF) energy. The catheter system further includes a proximal insert positioned partially within the catheter body and at least partially within the proximal end of the electrode tip body. The proximal insert includes a fluid inlet for receiving a cooling fluid delivered via the catheter body. The proximal insert forms a flow path configured to direct the cooling fluid from the fluid inlet to cool the distal portion of the catheter body and to cool a junction of the catheter body and the electrode tip body.

20 Claims, 4 Drawing Sheets

(51) Int. Cl.
   *A61B 18/00* (2006.01)
   *A61B 17/00* (2006.01)
(52) U.S. Cl.
   CPC .............. *A61B 2018/00011* (2013.01); *A61B 2018/00029* (2013.01); *A61B 2018/00065* (2013.01); *A61B 2018/00351* (2013.01); *A61B 2018/00577* (2013.01); *A61B 2018/00791* (2013.01); *A61B 2018/00821* (2013.01); *A61B 2218/002* (2013.01)
(58) Field of Classification Search
   CPC ........ A61B 18/00029; A61B 18/00011; A61B 5/6852
   See application file for complete search history.

(56) References Cited

U.S. PATENT DOCUMENTS

| | | | |
|---|---|---|---|
| 5,458,597 | A | 10/1995 | Edwards et al. |
| 5,545,161 | A | 8/1996 | Imran |
| 5,584,872 | A | 12/1996 | Lafontaine et al. |
| 5,643,197 | A | 7/1997 | Brucker et al. |
| 5,871,525 | A | 2/1999 | Edwards et al. |
| 5,895,355 | A | 4/1999 | Schaer |
| 5,932,035 | A | 8/1999 | Koger et al. |
| 6,013,052 | A | 1/2000 | Durman et al. |
| 6,053,912 | A | 4/2000 | Panescu et al. |
| 6,287,301 | B1 | 9/2001 | Thompson et al. |
| 7,628,788 | B2 | 12/2009 | Datta |
| 7,914,528 | B2 | 3/2011 | Wang et al. |
| 8,273,082 | B2 | 9/2012 | Wang et al. |
| 8,348,937 | B2 * | 1/2013 | Wang .................. A61B 18/18 606/41 |
| 8,517,999 | B2 | 8/2013 | Pappone et al. |
| 9,241,761 | B2 | 1/2016 | Rankin et al. |
| 9,445,725 | B2 | 9/2016 | Govari et al. |
| 9,456,867 | B2 * | 10/2016 | Lawrence .............. A61B 5/283 |
| 9,615,879 | B2 | 4/2017 | Kim et al. |
| 2003/0004506 | A1 | 1/2003 | Messing |
| 2003/0009094 | A1 | 1/2003 | Segner et al. |
| 2005/0203410 | A1 | 9/2005 | Jenkins |
| 2006/0074444 | A1 | 4/2006 | Lin et al. |
| 2006/0184165 | A1 | 8/2006 | Webster et al. |
| 2007/0270791 | A1 | 11/2007 | Wang et al. |
| 2008/0071267 | A1 | 3/2008 | Wang et al. |
| 2008/0147060 | A1 | 6/2008 | Choi |
| 2008/0161789 | A1 | 7/2008 | Thao et al. |
| 2008/0161792 | A1 | 7/2008 | Wang et al. |
| 2008/0161795 | A1 | 7/2008 | Wang et al. |
| 2008/0200801 | A1 | 8/2008 | Wildes et al. |
| 2008/0243214 | A1 | 10/2008 | Koblish |
| 2008/0249522 | A1 | 10/2008 | Pappone et al. |
| 2009/0093810 | A1 | 4/2009 | Subramaniam et al. |
| 2009/0093811 | A1 | 4/2009 | Koblish et al. |
| 2009/0125016 | A1 | 5/2009 | Wang et al. |
| 2009/0163913 | A1 | 6/2009 | Wang et al. |
| 2010/0030018 | A1 * | 2/2010 | Fortier .............. A61B 18/1445 600/104 |
| 2010/0168728 | A1 | 7/2010 | Wang et al. |
| 2010/0249601 | A1 | 9/2010 | Courtney |
| 2010/0331658 | A1 | 12/2010 | Kim et al. |
| 2011/0009857 | A1 | 1/2011 | Subramaniam et al. |
| 2011/0066144 | A1 * | 3/2011 | Bonn .................... A61B 18/18 606/33 |
| 2011/0201973 | A1 | 8/2011 | Stephens et al. |
| 2011/0224667 | A1 | 9/2011 | Koblish et al. |
| 2011/0264089 | A1 | 10/2011 | Zirkle et al. |
| 2011/0270046 | A1 | 11/2011 | Paul et al. |
| 2011/0270246 | A1 | 11/2011 | Clark et al. |
| 2012/0017287 | A1 | 1/2012 | Bumiller et al. |
| 2012/0035539 | A1 | 2/2012 | Tegg |
| 2012/0035605 | A1 | 2/2012 | Tegg et al. |
| 2012/0046610 | A1 | 2/2012 | Rankin |
| 2012/0165812 | A1 | 6/2012 | Christian |
| 2012/0172871 | A1 | 7/2012 | Hastings et al. |
| 2013/0137980 | A1 | 5/2013 | Waters et al. |
| 2014/0187893 | A1 | 7/2014 | Clark et al. |
| 2014/0276759 | A1 * | 9/2014 | Kim .................. A61B 18/1492 606/33 |
| 2015/0272669 | A1 * | 10/2015 | Brucker ............ A61B 18/1492 606/41 |

FOREIGN PATENT DOCUMENTS

| | | |
|---|---|---|
| EP | 1690510 A1 | 8/2006 |
| EP | 2380519 A1 | 10/2011 |
| JP | H11505747 A | 5/1999 |
| JP | 2011500156 A | 1/2011 |
| JP | 2011229918 A | 11/2011 |
| JP | 2012531967 A | 12/2012 |
| JP | 2012532737 A | 12/2012 |
| JP | 2014128674 A | 7/2014 |
| WO | 2009048824 A1 | 4/2009 |
| WO | 2009048943 A1 | 4/2009 |
| WO | 2014151876 A1 | 9/2014 |

OTHER PUBLICATIONS

International Preliminary Report on Patentability issued in PCT/US2014/026509, dated Sep. 24, 2015, 12 pages.
International Preliminary Report on Patentability issued in PCT/US2014/026602, dated Sep. 24, 2015, 10 pages.
International Search Report and Written Opinion issued in PCT/US2013/073461, dated Jun. 16, 2014, 15 pages.
International Search Report and Written Opinion issued in PCT/US2014/026509, dated Nov. 11, 2014, 16 pages.
International Search Report and Written Opinion issued in PCT/US2014/026602, dated Jun. 25, 2014, 12 pages.
International Search Report and Written Opinion issued in PCT/US2017/067146, dated Apr. 16, 2018, 11 pages.

* cited by examiner

OPEN-IRRIGATED ABLATION CATHETER WITH PROXIMAL INSERT COOLING

CROSS-REFERENCE TO RELATED APPLICATION

This application claims priority to Provisional Application No. 62/436,398, filed Dec. 19, 2016, which is herein incorporated by reference in its entirety.

TECHNICAL FIELD

The present disclosure pertains to medical devices. More particularly, the present disclosure pertains to techniques related to open-irrigated catheters used to perform ablation functions.

BACKGROUND

Aberrant conductive pathways disrupt the normal path of the heart's electrical impulses. For example, conduction blocks can cause the electrical impulse to degenerate into several circular wavelets that disrupt the normal activation of the atria or ventricles. The aberrant conductive pathways create abnormal, irregular, and sometimes life threatening heart rhythms called arrhythmias. Ablation is one way of treating arrhythmias and restoring normal contraction. The sources of the aberrant pathways (called focal arrhythmia substrates) are located or mapped using mapping electrodes situated in a desired location. After mapping, the physician may ablate the aberrant tissue. In radio frequency (RF) ablation, RF energy is directed from the ablation electrode through tissue to an electrode to ablate the tissue and form a lesion.

Heat is generated during the RF ablation process, and this heat may cause a thrombus (blood clot) or undesired charring of untargeted tissue. To control heat from the RF ablation process, open-irrigated catheters may cool the electrode and surrounding tissue using cooling fluid exiting the catheter through fluid apertures in the ablation electrode.

SUMMARY

The present disclosure relates to techniques for cooling electrodes and surrounding tissue in irrigated catheters, such as catheters used in RF ablation.

In Example 1, an open-irrigated ablation catheter system comprises: a catheter body; an electrode tip body mounted on a distal portion of the catheter body, the electrode tip body including a distal end and a proximal end, the proximal end configured for connection to the catheter body, the electrode tip body further including a central longitudinal axis and a wall defining an open interior region, the wall including one or more irrigation ports in fluid communication with the open interior region, wherein the wall is conductive for delivering radio frequency (RF) energy; and a proximal insert positioned partially within the catheter body and at least partially within the proximal end of the electrode tip body, wherein the proximal insert includes a fluid inlet for receiving a cooling fluid delivered via the catheter body, and wherein the proximal insert forms a flow path configured to direct the cooling fluid from the fluid inlet to cool the distal portion of the catheter body and to cool a junction of the catheter body and the electrode tip body.

In Example 2, the catheter system of Example 1, wherein an exterior surface of the proximal insert includes ribs forming channels between an interior surface of the proximal end of the electrode tip body and the exterior surface of the proximal insert, the channels being part of the flow path configured to direct the cooling fluid from the fluid inlet to cool the distal portion of the catheter body and to cool the junction of the catheter body and the electrode tip body.

In Example 3, the catheter system of Example 2, wherein all fluid flowing distally through the fluid inlet is directed through the channels between the interior surface of the proximal end of the electrode tip body and the exterior surface of the proximal insert.

In Example 4, the catheter system of Example 2, wherein the distal portion of the catheter body covers the proximal end of the electrode tip body.

In Example 5, the catheter system of Example 1, wherein the distal portion of the catheter body covers the proximal end of the electrode tip body, wherein the proximal insert is formed from a porous structure with open connected cells to promote heat exchange between the proximal insert and a cooling fluid, the porous structure being part of the flow path configured to direct the cooling fluid from the fluid inlet to cool the distal portion of the catheter body and to cool the junction of the catheter body and the electrode tip body.

In Example 6, the catheter system of Example 5, wherein the porous structure is a metal foam.

In Example 7, the catheter system of Example 5, wherein the distal portion of the catheter body covers the proximal end of the electrode tip body.

In Example 8, the catheter system of Example 1, wherein the proximal insert is configured to accept a steering line that facilitates bending the electrode tip body relative to the catheter body.

In Example 9, the catheter system of Example 1, further comprising a distal insert positioned within the electrode tip body, the distal insert separating the open interior region into a distal fluid chamber and a proximal fluid chamber, the distal insert including an opening fluidly connecting the distal and proximal fluid chambers, wherein the fluid inlet is in fluid communication with the distal fluid chamber.

In Example 10, the catheter system of Example 9, wherein the distal end of the electrode tip body is closed and the proximal end of the electrode tip body is open.

In Example 11, the catheter system of Example 10, further comprising a thermocouple, wherein the distal insert includes an opening sized to receive the thermocouple, wherein the thermocouple extends through the proximal and distal inserts such that a distal end of the thermocouple is disposed adjacent the closed distal end of the electrode tip body.

In Example 12, the catheter system of Example 9, further comprising one or more mapping electrodes.

In Example 13, the catheter system of Example 12, wherein the distal insert includes one or more openings therein sized to receive the one or more mapping electrodes.

In Example 14, the catheter system of Example 1, wherein the catheter body covers a swaged portion of the electrode tip body, with the junction of the catheter body and the electrode tip body being proximate to a distal edge of the swaged portion of the electrode tip body.

In Example 15, the catheter system of Example 1, wherein the catheter body is formed from an electrically insulating and thermally insulating material.

In Example 16, an open-irrigated ablation catheter system comprises: a catheter body; an electrode tip body mounted on a distal portion of the catheter body, the electrode tip body including a distal end and a swaged proximal end configured for connection to a distal end of the catheter body, the electrode tip body further including a central longitudinal axis and a wall defining an open interior region, the wall including one or more irrigation ports in fluid communication with the open interior region, wherein the wall is conductive for delivering radio frequency (RF) energy; and a proximal insert positioned partially within the catheter body and at least partially within the swaged proximal end of the electrode tip body, wherein the proximal insert includes a fluid inlet for receiving a cooling fluid delivered via the catheter body, and wherein an exterior surface of the proximal insert includes ribs forming channels between an interior surface of the proximal end of the electrode tip body and the exterior surface of the proximal insert, the channels being configured to direct the cooling fluid from the fluid inlet to cool the distal portion of the catheter body and to cool a junction of the catheter body and the electrode tip body.

In Example 17, the catheter system of Example 16, wherein all fluid flowing distally through the fluid inlet is directed through the channels between the interior surface of the proximal end of the electrode tip body and the exterior surface of the proximal insert.

In Example 18, the catheter system of Example 16, wherein the distal portion of the catheter body covers the swaged proximal end of the electrode tip body such that the junction of the catheter body and the electrode tip body is proximate to a distal edge of the swaged proximal end of the electrode tip body.

In Example 19, an open-irrigated ablation catheter system, comprises: a catheter body; an electrode tip body mounted on a distal portion of the catheter body, the electrode tip body including a distal end and a swaged proximal end configured for connection to a distal end of the catheter body, the electrode tip body further including a central longitudinal axis and a wall defining an open interior region, the wall including one or more irrigation ports in fluid communication with the open interior region, wherein the wall is conductive for delivering radio frequency (RF) energy; and a proximal insert positioned partially within the catheter body and at least partially within the swaged proximal end of the electrode tip body, wherein the proximal insert includes a fluid inlet for receiving a cooling fluid delivered via the catheter body, and wherein the proximal insert is includes a porous structure with open connected cells to promote heat exchange between the proximal insert and a cooling fluid at a junction of the catheter body and the electrode tip body the porous structure extending both proximally and distally relative to the junction of the catheter body and the electrode tip body.

In Example 20, the catheter system of Example 19, wherein the porous structure is a metal foam.

In Example 21, an open-irrigated ablation catheter system, comprises: a catheter body; an electrode tip body mounted on a distal portion of the catheter body, the electrode tip body including a distal end and a proximal end, the proximal end configured for connection to the catheter body, the electrode tip body further including a central longitudinal axis and a wall defining an open interior region, the wall including one or more irrigation ports in fluid communication with the open interior region, wherein the wall is conductive for delivering radio frequency (RF) energy; and a proximal insert positioned partially within the catheter body and at least partially within the proximal end of the electrode tip body, wherein the proximal insert includes a fluid inlet for receiving a cooling fluid delivered via the catheter body, and wherein the proximal insert forms a flow path configured to direct the cooling fluid from the fluid inlet to cool the distal portion of the catheter body and to cool a junction of the catheter body and the electrode tip body.

In Example 22, the catheter system of Example 21, wherein an exterior surface of the proximal insert includes ribs forming channels between an interior surface of the proximal end of the electrode tip body and the exterior surface of the proximal insert, the channels being part of the flow path configured to direct the cooling fluid from the fluid inlet to cool the distal portion of the catheter body and to cool the junction of the catheter body and the electrode tip body.

In Example 23, the catheter system of Example 22, wherein all fluid flowing distally through the fluid inlet is directed through the channels between the interior surface of the proximal end of the electrode tip body and the exterior surface of the proximal insert.

In Example 24, the catheter system of Examples 22 or 23, wherein the distal portion of the catheter body covers the proximal end of the electrode tip body.

In Example 25, the catheter system of Example 21, wherein the distal portion of the catheter body covers the proximal end of the electrode tip body, wherein the proximal insert is formed from a porous structure with open connected cells to promote heat exchange between the proximal insert and a cooling fluid, the porous structure being part of the flow path configured to direct the cooling fluid from the fluid inlet to cool the distal portion of the catheter body and to cool the junction of the catheter body and the electrode tip body.

In Example 26, the catheter system of Example 25, wherein the porous structure is a metal foam.

In Example 27, the catheter system of Examples 25 or 26, wherein the distal portion of the catheter body covers the proximal end of the electrode tip body.

In Example 28, the catheter system any of Examples 21 to 27, wherein the proximal insert is configured to accept a steering line that facilitates bending the electrode tip body relative to the catheter body.

In Example 29, the catheter system any of Examples 21 to 28, further comprising a distal insert positioned within the electrode tip body, the distal insert separating the open interior region into a distal fluid chamber and a proximal fluid chamber, the distal insert including an opening fluidly connecting the distal and proximal fluid chambers, wherein the fluid inlet is in fluid communication with the distal fluid chamber.

In Example 30, the catheter system of Example 29, wherein the distal end of the electrode tip body is closed and the proximal end of the electrode tip body is open.

In Example 31, the catheter system of Examples 29 or 30, further comprising a thermocouple, wherein the distal insert includes an opening sized to receive the thermocouple, wherein the thermocouple extends through the proximal and distal inserts such that a distal end of the thermocouple is disposed adjacent the closed distal end of the electrode tip body.

In Example 32, the catheter system of any of Examples 29 to 31, further comprising one or more mapping electrodes.

In Example 33, the catheter system of Example 32, wherein the distal insert includes one or more openings therein sized to receive the one or more mapping electrodes.

In Example 34, the catheter system of any of Examples 21 to 33, wherein the catheter body covers a swaged portion of the electrode tip body, with the junction of the catheter body and the electrode tip body being proximate to a distal edge of the swaged portion of the electrode tip body.

In Example 35, the catheter system of any of Examples 21 to 34, wherein the catheter body is formed from an electrically insulating and thermally insulating material.

While multiple examples are disclosed, still other examples of the present disclosure will become apparent to those skilled in the art from the following detailed description, which shows and describes illustrative examples of the disclosure. Accordingly, the drawings and detailed description are to be regarded as illustrative in nature and not restrictive.

Figure 1:
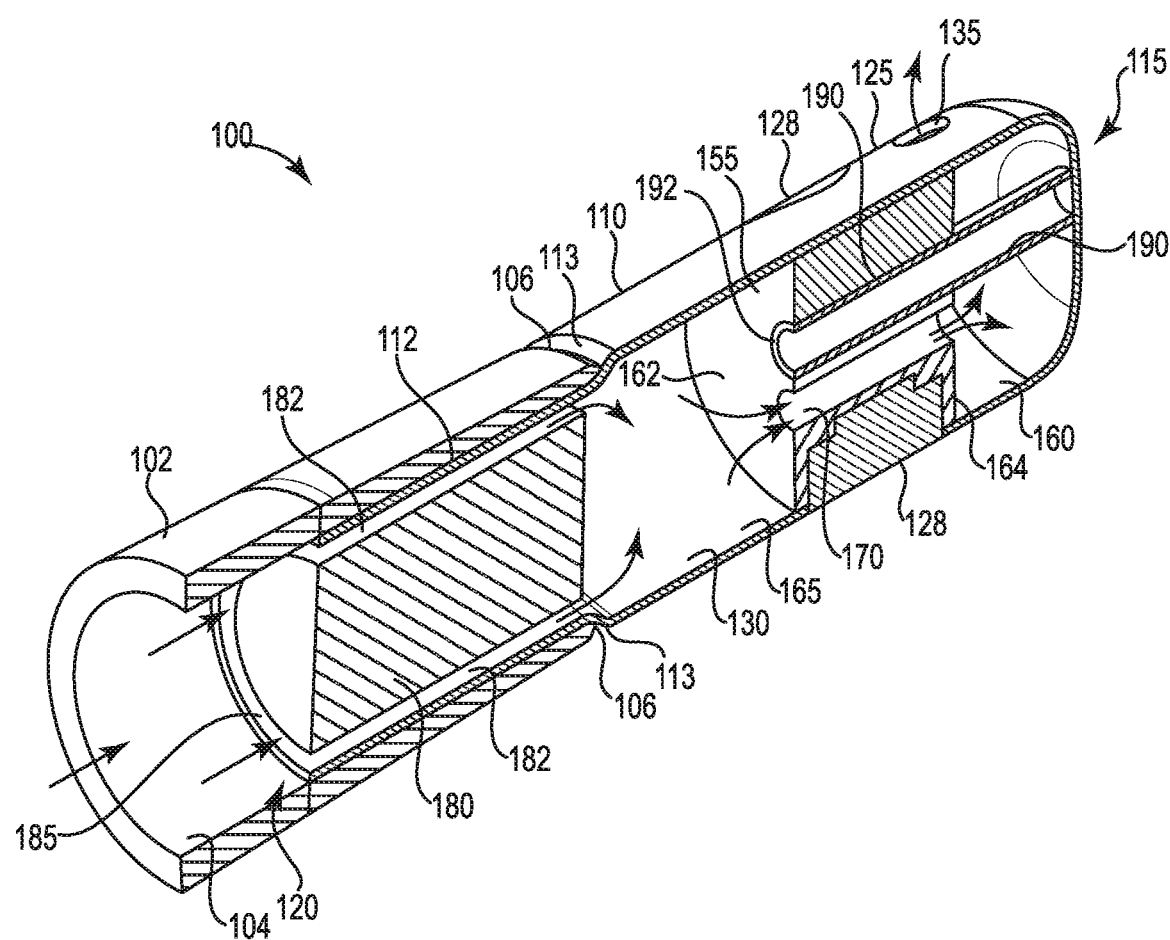
FIG. 1 illustrates the distal end of an open-irrigated catheter including a proximal insert forming a flow path configured to direct cooling fluid to cool a junction of the catheter body and the electrode tip body.

While the disclosure is amenable to various modifications and alternative forms, specific examples have been shown by way of example in the drawings and are described in detail below. The intention, however, is not to limit the disclosure to the particular examples described. On the contrary, the disclosure is intended to cover all modifications, equivalents, and alternatives falling within the scope of the disclosure as defined by the appended claims.

DETAILED DESCRIPTION

Open-irrigated cardiac ablation catheters with low irrigation flow rate (low flow) are desirable to limit the volume of saline delivered to the patient during ablation especially with long procedures where multiple RF applications are performed. However, low irrigation flow rates may increase risk of thrombus and char formation.

This disclosure generally relates to an open-irrigated RF ablation catheter system. This disclosure describes techniques to improve the internal cooling inside the tip electrode for open-irrigated ablation catheters to allow the use of lower irrigation flow rates or enhance the safety profile at currently-used flow rates.

As disclosed herein, open-irrigated RF ablation catheters are configured to direct cooling fluid flowing within a distal tip electrode to cool a junction of the catheter body and an electrode tip body and thereby to improve the uniformity of cooling of the distal end of the catheter. Because the junction of the catheter body and an electrode tip body may represent a localized hot spot, the disclosed open-irrigated RF ablation catheters may improve the uniformity of cooling at the distal end of the catheter and decrease the risk of thrombus formation.

Figure 2:
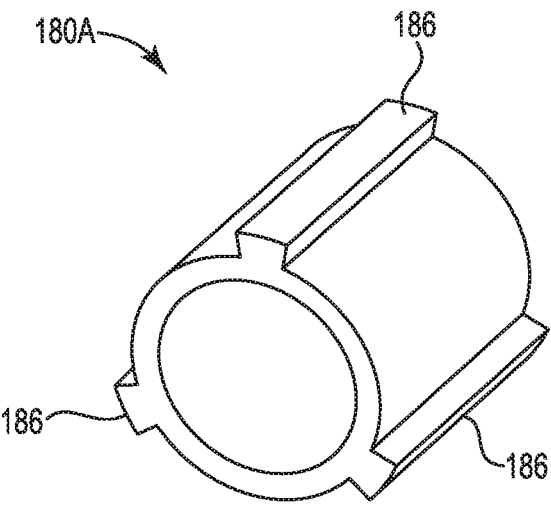
FIGS. 2A-2C illustrate example proximal inserts suitable for use as part of the open-irrigated catheter of FIG. 1, the example proximal inserts each including ribs forming cooling channels configured to cool the junction of the catheter body and electrode tip body.
Figure 2:
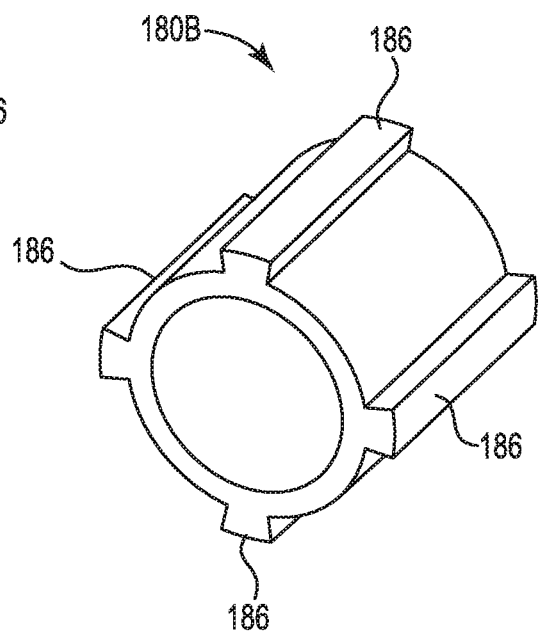
Figure 2:
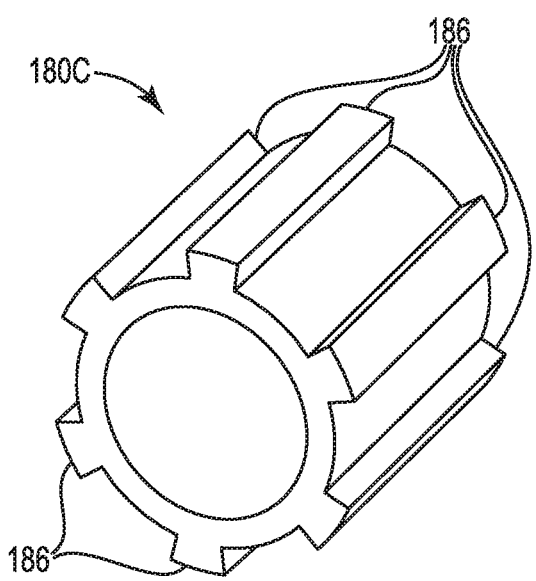

FIG. 1 illustrates the distal end of an open-irrigated catheter system 100 including a catheter body 102 with a lumen 104, an electrode tip body 110 mounted on a distal portion of catheter body 102, a proximal insert 180, a distal insert 155, and a thermocouple 190. Proximal insert 180 forms a flow path configured to direct cooling fluid to cool a junction 106 between catheter body 102 and electrode tip body 110. FIGS. 2A-2C illustrate example proximal inserts 180A, 180B, 180C suitable for use as part of the open-irrigated catheter of FIG. 1, proximal inserts 180A, 180B, 180C each include ribs 186 that combine with the interior surface of electrode tip body 110 to form cooling channels configured to cool junction 106 of catheter body 102 and electrode tip body 110.

Electrode tip body 110 is generally hollow with a closed distal end 115, an open interior region 130, and an open proximal end 120. In the illustrated example, the hollow electrode tip body 110 has a generally cylindrical shape. Electrode tip body 110 may include one or more openings or irrigation ports 135 and one or more openings 128 for receiving electrodes such as mapping electrodes.

Electrode tip body 110 includes a swaged portion 112 that slides inside a distal end of catheter body 102 such that the distal portion of the catheter body 102 covers the proximal end of the electrode tip body 110, thereby mounting the electrode tip body 110 to the distal end the catheter body 102.

Catheter body 102 may be formed from an electrically insulating and thermally insulating material, such as, for example, a Pellethane tube. Proximal insert 180 may be made of high thermal conductivity metals such as, by way of example, but not limitation, silver, platinum, gold, stainless steel, plated brass, platinum iridium and combinations thereof. The high electric conductivity of electrode tip body 110, which may be for example, a platinum-iridium alloy, contrasted with the low electric conductivity of the catheter body 102 results in an "edge effect" at the junction 106 of the electrode tip body 110 and catheter body 102. This edge effect combined with the low radius of curvature existing on the edge 113 of swaged portion 112 may give rise to a high RF power deposition density distribution near junction 106 during ablation. Combined with the relatively low thermal conductivity of catheter body 102, this edge effect may produce relatively high temperatures near junction 106. Open-irrigated catheter system 100 mitigates these high temperatures by directing cooling fluid to cool both junction 106 between catheter body 102 and electrode tip body 110 and a distal portion of catheter body 102 proximal to junction 106.

Proximal insert 180 fits into the open proximal end 120 of the electrode tip body 110. Specifically, proximal insert 180 fits within swaged portion 112 of electrode tip body 110. Proximal insert 180 may have any shape and dimension provided at least a portion of the proximal insert fits within the open proximal end 120 of the electrode tip body 110. Proximal insert 180 may be configured to accept a steering line (not shown) that facilitates remotely bending electrode tip body 110 relative to catheter body 102.

Cooling fluid can be delivered through the lumen 104 of the catheter body 102, through the lumen 182 of the proximal insert 180 and into the open interior region 130 of the electrode tip 110. Specifically, proximal insert 180 forms a generally annular gap 182 between an exterior surface of proximal insert 180 and an interior surface of swaged portion 112 of electrode tip body 110.

FIGS. 2A-2C illustrate example proximal inserts 180A, 180B and 180C that are each suitable for use as proximal insert 180. As shown in the examples of FIGS. 2A-2C, proximal insert 180 may include ribs 186 forming channels between an interior surface of the proximal end of the electrode tip body 100 and the exterior surface of the proximal insert 180. Within open-irrigated catheter system 100 ribs 186 are configured to register with thin inner diameter of swaged portion 112 of electrode tip body 110.

Annular gap 182 (FIG. 1) is formed by the channels is part of the flow path configured to direct the cooling fluid from fluid inlet 185 to cool the distal portion of catheter body 102 and to cool junction 106 between catheter body 102 and electrode tip body 110. For example, fluid inlet 185 may be a port that connects to a fluid delivery tube (not shown) within lumen 104 of the catheter body 102, or catheter body 102 itself may serve as a fluid delivery tube. In some examples, all fluid flowing distally through fluid inlet 185 may be directed through the channels between the interior surface of the swaged portion 112 of the electrode tip body and the exterior surface of the proximal insert 180. The flow of cooling fluid provides cooling for the distal portion of catheter body 102 and for cool junction 106 between catheter body 102 and electrode tip body 110 as the fluid flows through annular gap 182 into the open interior region 130 of the electrode tip body 110. The decrease in temperature adjacent junction 113 reduces the likelihood that the tissue surrounding junction 113 or the distal end of catheter body 102 will char and/or that coagulum will form on the surface of the electrode tip body or catheter body 102 adjacent junction 113.

A distal insert 155 divides the open interior region 130 of the electrode tip body 110 into a distal fluid reservoir 160 and a proximal fluid reservoir 165, each of which act as cooling chambers. The distal insert 155 may be a thermal mass. The distal insert 155 has an opening 170 extending from a proximal surface 162 of the distal insert to a distal surface 164. The opening 170 fluidly connects the distal fluid reservoir 160 and the proximal fluid reservoir 165, allowing cooling fluid to flow therethrough. One or more irrigation ports 135 through the wall 125 of the electrode tip body 110 near the distal end 115 allows cooling fluid to exit the device and cool the tip and surrounding tissues. If more than one irrigation port is present, the irrigation ports 135 may be equally spaced around the circumference of the electrode tip body. However, the present subject matter is not limited to equally-spaced irrigation ports or to a particular number of irrigation ports. The system can be designed with other numbers and arrangements of irrigation ports. The catheter system may include a temperature sensor mounted within the electrode tip body 110. In the illustrated example, the temperature sensor is a thermocouple 190 that extends through an opening 192 in the distal insert 155.

The cooling fluid cools both the electrode tip body 110 and the tissue adjacent to the perimeter of the electrode tip body. For example, the cooling fluid draws heat from the electrode tip body 110 (including the thermal mass distal insert 155) and reduces the temperature of the electrode. The presence of the proximal fluid reservoir 165, the distal insert 155, and distal fluid reservoir 160 augments the fluid cooling because the fluid flows along the wall 125 and into the proximal fluid reservoir 165 where it circulates prior to entering the distal fluid reservoir 160, where the fluid again circulates prior to exiting the electrode tip body 110 by way of the irrigation ports 135. The decrease in electrode and tissue temperature reduces the likelihood that the tissue in contact with the electrode tip body 110 will char and/or that coagulum will form on the surface of the electrode tip body. In addition to cooling tissue adjacent to the electrode tip body 110, fluid that exits the electrode tip body sweeps biological material such as blood and tissue away from the electrode, further reducing the likelihood of coagulum formation.

Figure 3A:
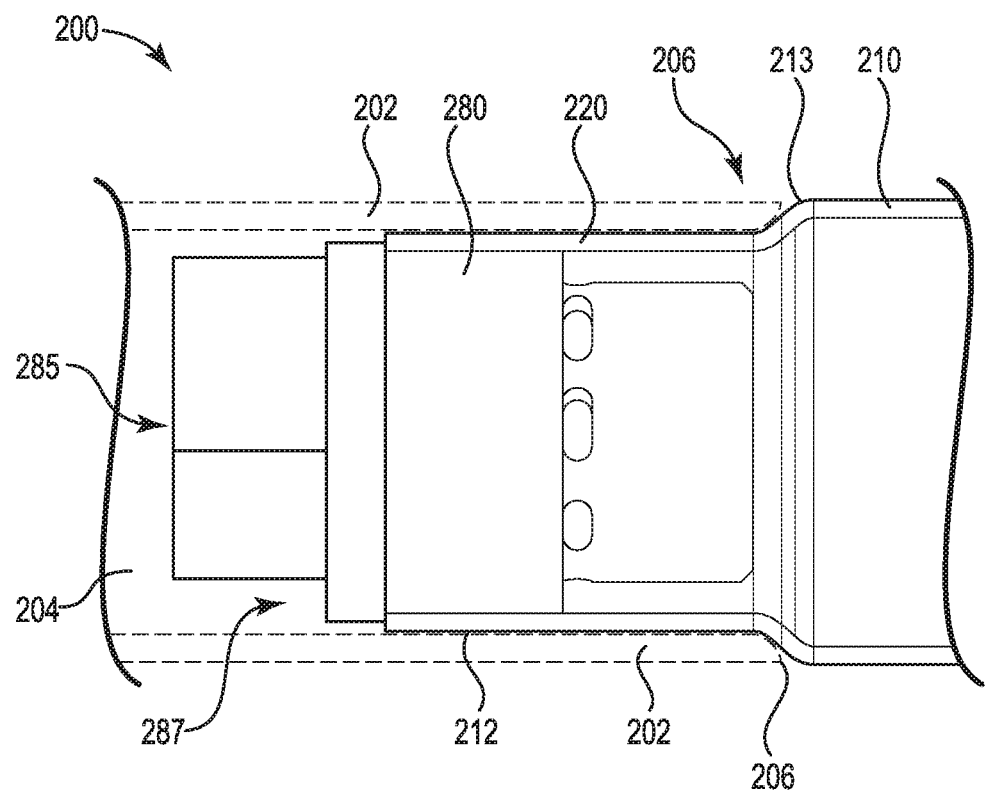
FIGS. 3A and 3B illustrate a distal portion of an open-irrigated catheter system including a proximal insert including a porous/lattice structure configured to direct cooling fluid to cool a junction of the catheter body and electrode tip body.
Figure 3B:
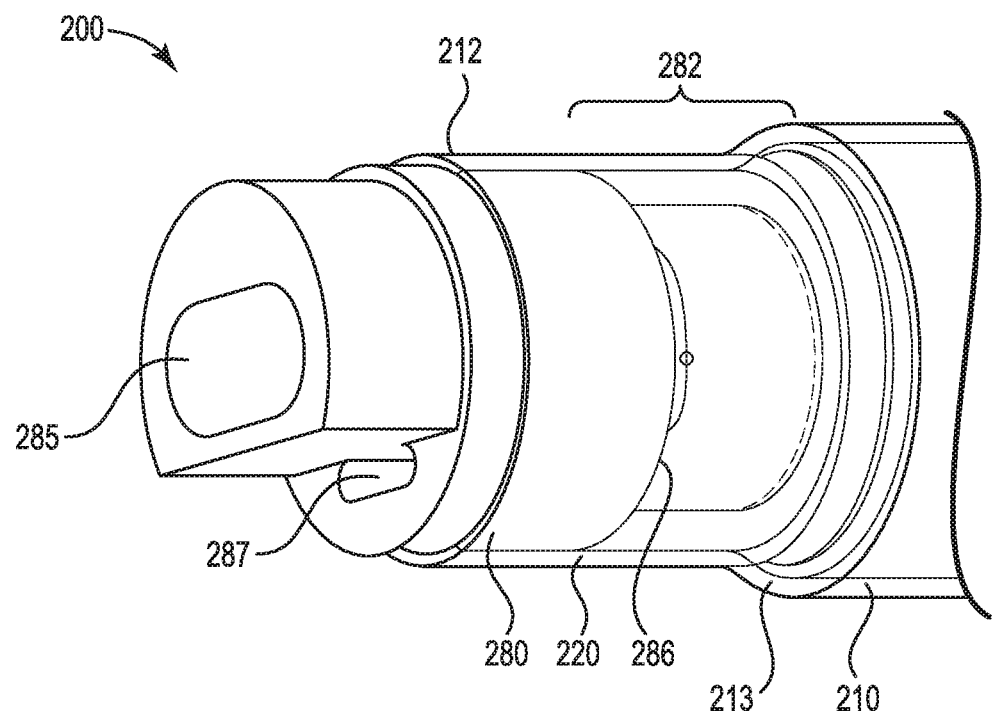
Figure 4:
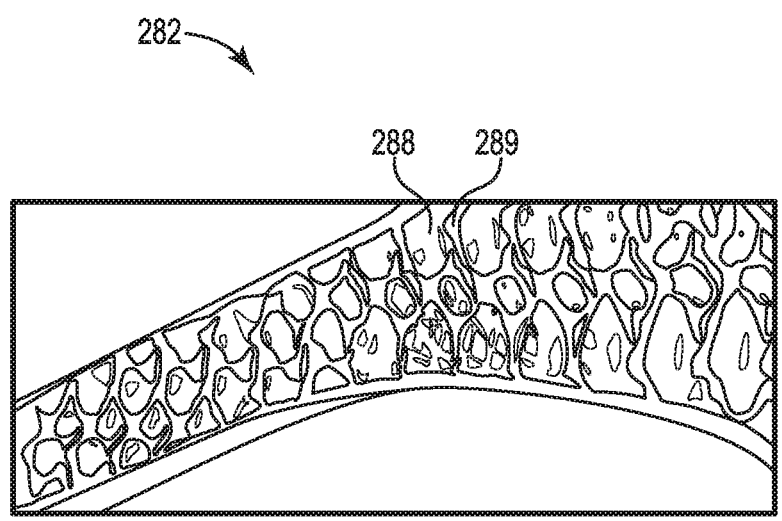
FIG. 4 illustrates an example porous/lattice structure suitable for use as part of the open-irrigated catheter of FIGS. 3A and 3B.

FIGS. 3A and 3B illustrate a distal portion of an open-irrigated catheter system 200 including a proximal insert 280 including a porous/lattice structure 282 configured to direct cooling fluid to cool a junction 206 of the catheter body 202 and electrode tip body 210. FIG. 4 illustrates an example porous/lattice structure suitable 282 for use as part of proximal insert 280 of the open-irrigated catheter system 200.

Only a portion of open-irrigated catheter system 200 is shown in FIGS. 3A and 3B; however, open-irrigated catheter system 200 is substantially similar to open-irrigated catheter system 100 except that proximal insert 280 including porous/lattice structure 282 instead of ribs 186. Like ribs 186, porous/lattice structure 282 is configured to direct cooling fluid from a fluid inlet port (285) to form a cooling zone 286 to cool the distal portion of the catheter body (202) and to cool a junction (213) of the catheter body (202) and the electrode tip body (210). In this manner, proximal insert 280 forms a flow path configured to direct cooling fluid to cool a junction 206 between catheter body 202 and electrode tip body 210.

As shown in FIG. 4, porous/lattice structure 282 includes a combination of structural elements 288 and voids 289. Voids 289 form the flow path for a cooling fluid, whereas structural elements 288 provide thermal conductive pathways between the cooling fluid and the external surfaces of proximal insert 280. In some examples, porous/lattice structure 282 is a metal foam with open connected cells (with high surface area per unit volume) to promote heat exchange between proximal insert 280 and cooling fluid. In different examples, porous/lattice structure 282 may be formed using processes such as additive manufacturing, sintering, infiltration processing, casting etc. The pore structure can be regular or irregular.

As open-irrigated catheter system 200 is substantially similar to open-irrigated catheter system 100, other than the replacement of proximal insert 180 with proximal insert 280 details of open-irrigated catheter system 200 already described with respect to open-irrigated catheter system 100 are described in limited or no detail.

Electrode tip body 210 includes a swaged portion 212 that slides inside a distal end of catheter body 202, which may be, for example, a Pellethane tube. The high electric conductivity of electrode tip body 210, which may be for example, a platinum-iridium alloy contrasted with the low electric conductivity of Pellethane results in an "edge effect" at the junction 206 of the electrode tip body 210 and catheter body 202. This edge effect combined with the low radius of curvature existing on the edge 213 of swaged portion 212 give rise to a high RF power deposition density distribution near that region during ablation. Combined with the relatively low thermal conductivity of catheter body 202, this edge effect may produce relatively high temperatures near junction 206. Open-irrigated catheter system 200 mitigates these high temperatures by directing cooling fluid to cool junction 206 between catheter body 202 and electrode tip body 210.

Proximal insert 280 fits into the open proximal end 220 of the electrode tip body 210. Specifically, proximal insert 280 fits within swaged portion 212 of electrode tip body 210. Proximal insert 280 may have any shape and dimension provided at least a portion of the proximal insert fits within the open proximal end 220 of the electrode tip body 210. Proximal insert 280 is configured to accept a steering line (not shown) via steering attachment feature 287. The steering line facilitates bending electrode tip body 210 relative to catheter body 202.

Cooling fluid can be delivered through the lumen 204 of the catheter body 202, optionally within a fluid delivery tube (not shown) within lumen 204 of the catheter body 202, through fluid inlet port 285 and through porous/lattice structure 282 and into an open interior region of the electrode tip body 210. Porous/lattice structure 282 may be made of a material with high thermal conductivity such heat is transferred between proximal insert 280 and the cooling fluid such that an external surface of proximal insert 280, a distal end of catheter body 202 and junction 213 is cooled from the flow of the cooling fluid. The decrease in temperature adjacent junction 213 reduces the likelihood that the tissue surrounding junction 213 will char and/or that coagulum will form on the surface of the electrode tip body adjacent junction 213.

In some examples, open-irrigated catheters, such as open-irrigated catheter systems 100, 200, may be used within body lumens, chambers or cavities for diagnostic or therapeutic purposes in those instances where access to interior bodily regions is obtained through, for example, the vascular system or alimentary canal and/or with minimally invasive surgical procedures. For example, some examples have application in the diagnosis and treatment of arrhythmia conditions within the heart. Some examples also have application in the diagnosis or treatment of ailments of the gastrointestinal tract, prostrate, brain, gall bladder, uterus, and other regions of the body. With regard to the treatment of conditions involving the heart, some examples can be used to create lesions to treat atrial fibrillation, atrial flutter and ventricular tachycardia. Additionally, some examples can be used to modulate, block, or ablate nerve bodies in the treatment of neural structures. For example, some examples have application in the treatment of congestive heart failure, hypertension, and other cardio-renal diseases. With regard to the treatment of cardio-renal diseases, some examples can be used to modulate neural function of the renal nerve.

In some examples, open-irrigated catheters, such as open-irrigated catheter systems 100, 200, may be referred to as a hybrid catheters usable simultaneously for both localized mapping and ablation functions. However, not all examples would necessarily include both the mapping and ablation functions, and may instead incorporate only one or the other function. The hybrid catheter is configured to provide localized, high resolution ECG signals during ablation. The localized mapping enables the mapping to be more precise than that which can be achieved with conventional ablation catheters. The hybrid catheter has an open-irrigated catheter design. A cooling fluid, such as a saline, is delivered through the catheter to the catheter tip, where the fluid exits through irrigation ports to cool the electrode and surrounding tissue. Clinical benefits of such a catheter include, but are not limited to, controlling the temperature and reducing coagulum formation on the tip of the catheter, preventing impedance rise of tissue in contact with the catheter tip, and maximizing potential energy transfer to the tissue. Additionally, the localized intra cardiac electrical activity can be recorded in real time or near-real time right at the point of energy delivery.

For example, catheter systems 100, 200 may be part of a mapping and ablation system that includes an open-irrigated catheter. Such catheters may be functionally divided into four regions: the operative distal probe assembly region (e.g. the distal portion of catheter body 102, 202), a main catheter region (not shown), a deflectable catheter region (not shown), and a proximal catheter handle region (not shown) where a handle assembly (not shown) is attached. The catheter body includes a coolant flow path or conduit and may include other tubular element(s) to provide the desired functionality to the catheter. The addition of metal in the form of a braided mesh layer (not shown) sandwiched in between layers of plastic tubing may be used to increase the rotational stiffness of the catheter.

Although the present examples are not so limited, the exemplary catheter is configured for use within the heart and, accordingly, is about 5 French to about 11 French (about 1.67 mm to about 3.67 mm) in diameter. The wall thickness of the exemplary electrode tip body may be about 0.05 mm to about 0.3 mm. The portion of the catheter that is inserted into the patient is typically from about 60 to 160 cm in length. The length and flexibility of the catheter allow the catheter to be inserted into a main vein or artery (typically the femoral vein), directed into the interior of the heart, and then manipulated such that the desired electrode(s) contact the target tissue. Fluoroscopic imaging may be used to provide the physician with a visual indication of the location of the catheter.

By way of an example and not limitation, the disclosed electrode tip bodies may have a diameter on the order of about 0.08-0.1 inches (about 0.2032-0.254 cm), a length on the order of about 0.2-0.3 inches (about 0.508-0.762 cm), and an exterior wall with a thickness on the order of 0.003-0.004 inches (0.00762-0.01016 cm). The distal end may be planar. It should be noted that there are no holes in the distal end wall of the exemplary electrode tip body for fluid cooling and/or passage of a temperature sensor that is aligned with the outer surface of the electrode. Such holes would create regions of high current density and regions of high current density near the center of the electrode tip would work against efforts to move current to the outer perimeter of the electrode tip.

By way of an example and not limitation, the disclosed irrigation ports may provide a diameter approximately within a range of 0.01 to 0.02 inches (0.0254 to 0.0508 cm). Fluid, such as a saline solution, flows from the distal fluid reservoir, through these ports to the exterior of the catheter. This fluid is used to cool the ablation electrode tip body and the tissue near the electrode. This temperature control reduces coagulum formation on the tip of the catheter, prevents impedance rise of tissue in contact with the catheter tip, and increases energy transfer to the tissue because of the lower tissue impedance.

With respect to material, the exemplary electrode tip bodies may be formed from any suitable electrically conductive material. By way of example, but not limitation, suitable materials for the main portion of the electrode tip body, i.e. the side wall and planar distal end, include silver, platinum, gold, stainless steel, plated brass, platinum iridium and combinations thereof. For example, some examples use a platinum-iridium alloy. Some examples use an alloy with approximately 90% platinum and 10% iridium. This conductive material is used to conduct RF energy used to form lesions during the ablation procedure. In examples of the electrode tip having a main body region with a larger diameter than a proximal region with a shoulder region therebetween, the reduction in diameter may be achieved by swaging. Alternatively, separate pieces of differing diameter may be laser welded or soldered together to form the electrode tip body.

By way of an example and not limitation, the disclosed distal inserts may be a thermal mass formed from any suitable electrically and thermally conducting material such as, for example, brass, copper and stainless. The distal insert may, alternatively, be made of thermally conducting and electrically non-conducing materials.

By way of an example and not limitation, the disclosed proximal inserts may be mounted within the proximal region of the electrode tip body. The proximal insert may be formed from an electrically conductive material such as stainless steel, or an electrically non-conductive material such as nylon or polyimide. The proximal insert may include any number of lumens for fluid flow and for receiving a thermocouple, steering element, electrical conductor, or other element. Alternatively, a fluid conduit may be placed within one of the lumens. A steering center support may be positioned within a lumen and be secured to the proximal insert.

A deflectable catheter region allows the catheter to be steered through the vasculature of the patient and allows the probe assembly to be accurately placed adjacent the targeted tissue region. A steering wire (not shown) may be slidably disposed within the catheter body. A handle assembly (not shown) may include a steering member such as a rotating steering knob that is rotatably mounted to the handle. Rotational movement of the steering knob relative to the handle in a first direction may cause a steering wire to move proximally relative to the catheter body which, in turn, tensions the steering wire, thus pulling and bending the catheter deflectable region into an arc; and rotational movement of the steering knob relative to the handle in a second direction may cause the steering wire to move distally relative to the catheter body which, in turn, relaxes the steering wire, thus allowing the catheter to return toward its form. To assist in the deflection of the catheter, the deflectable catheter region may be made of a lower durometer plastic than the main catheter region.

The disclosed catheter systems may include an RF generator (not shown) used to generate the energy for the ablation procedure. An RF generator may include a source for the RF energy and a controller for controlling the timing and the level of the RF energy delivered through the electrode tip body. The disclosed systems may include a fluid reservoir and pump (not shown) for pumping cooling fluid, such as a saline, through the catheter and out through the irrigation ports. A mapping signal processor (not shown) may be connected to the mapping electrodes. The mapping signal processor and mapping electrodes detect electrical activity of the heart. This electrical activity is evaluated to analyze an arrhythmia and to determine where to deliver the ablation energy as a therapy for the arrhythmia. One of ordinary skill in the art will understand that, the modules and other circuitry shown and described herein can be implemented using software, hardware, and/or firmware. Various disclosed methods may be implemented as a set of instructions contained on a computer-accessible medium capable of directing a processor to perform the respective method. Additional details concerning this type of catheter system may be found in, for example, U.S. Publication. Nos. 2008/0243214, 2009/0093810, 2010/0331658, and 2011/0009857, which are hereby incorporated by reference.

With respect to steering, the exemplary catheter systems 100, 200 may be provided with a conventional steering mechanism. For example, the catheter may include a steering wire (not shown) slidably disposed within the catheter body, or a steering center support and steering wire arrangement (not shown). A steering center support with a pair of adjacent steering wires may extend through the catheter body to a handle (not shown), which is also configured for steering. Additional details concerning this type of steering arrangement may be found in, for example, U.S. Pat. Nos. 5,871,525 and 6,287,301, which are hereby incorporated by reference. Other suitable steering arrangements are disclosed in U.S. Pat. Nos. 6,013,052 and 6,287,301, which are hereby incorporated by reference. Nevertheless, it should be noted that the present inventions are not limited to steerable catheter apparatus, or to any particular type of steering arrangement in those catheter apparatus which are steerable.

Various modifications and additions can be made to the examples discussed without departing from the scope of the present disclosure. For example, while the examples described above refer to particular features, the scope of this disclosure also includes examples including different combinations of features and examples that do not include all of the described features. Accordingly, the scope of the present disclosure is intended to embrace all such alternatives, modifications, and variations as fall within the scope of the claims, together with all equivalents thereof.

What is claimed is:

1. An open-irrigated ablation catheter system, comprising:
a catheter body;
an electrode tip body mounted on a distal portion of the catheter body, the electrode tip body including a distal end and a proximal end, the proximal end configured for connection to the catheter body, the electrode tip body further including a central longitudinal axis and a wall defining an open interior region, the wall including one or more irrigation ports in fluid communication with the open interior region,
wherein the wall is conductive for delivering radio frequency (RF) energy; and
a proximal insert positioned partially within the catheter body and at least partially within the proximal end of the electrode tip body,
wherein the proximal insert includes a fluid inlet for receiving a cooling fluid delivered via the catheter body, and an exterior surface along an entire longitudinal length of the proximal insert, and
wherein the external surface of the proximal insert and an interior surface of the proximal end of the electrode tip body form an annular gap extending the entire longitudinal length of the proximal insert, the annular gap defining a flow path configured to direct the cooling fluid from the fluid inlet to cool the distal portion of the catheter body and to cool a junction of the catheter body and the electrode tip body.

2. The catheter system of claim 1,
wherein the exterior surface of the proximal insert includes ribs forming channels between the interior surface of the proximal end of the electrode tip body and the exterior surface of the proximal insert, the channels forming of the flow path configured to direct the cooling fluid from the fluid inlet to cool the distal portion of the catheter body and to cool the junction of the catheter body and the electrode tip body.

3. The catheter system of claim 2, wherein all fluid flowing distally through the fluid inlet is directed through the channels between the interior surface of the proximal end of the electrode tip body and the exterior surface of the proximal insert.

4. The catheter system of claim 2, wherein the distal portion of the catheter body covers the proximal end of the electrode tip body.

5. The catheter system of claim 1,
wherein the distal portion of the catheter body covers the proximal end of the electrode tip body,
wherein the proximal insert is formed from a porous structure with open connected cells to promote heat exchange between the proximal insert and a cooling fluid, the porous structure being part of the flow path configured to direct the cooling fluid from the fluid inlet to cool the distal portion of the catheter body and to cool the junction of the catheter body and the electrode tip body.

6. The catheter system of claim 5, wherein the porous structure is a metal foam.

7. The catheter system of claim 5, wherein the distal portion of the catheter body covers the proximal end of the electrode tip body.

8. The catheter system of claim 1, wherein the proximal insert is configured to accept a steering line that facilitates bending the electrode tip body relative to the catheter body.

9. The catheter system of claim 1, further comprising a distal insert positioned within the electrode tip body, the distal insert separating the open interior region into a distal fluid chamber and a proximal fluid chamber, the distal insert including an opening fluidly connecting the distal and proximal fluid chambers, wherein the fluid inlet is in fluid communication with the distal fluid chamber.

10. The catheter system of claim 9, wherein the distal end of the electrode tip body is closed and the proximal end of the electrode tip body is open.

11. The catheter system of claim 10, further comprising a thermocouple, wherein the distal insert includes an opening sized to receive the thermocouple, wherein the thermocouple extends through the proximal and distal inserts such that a distal end of the thermocouple is disposed adjacent the closed distal end of the electrode tip body.

12. The catheter system of claim 9, further comprising one or more mapping electrodes.

13. The catheter system of claim 12, wherein the distal insert includes one or more openings therein sized to receive the one or more mapping electrodes.

14. The catheter system of claim 1, wherein the catheter body covers a swaged portion of the electrode tip body, with the junction of the catheter body and the electrode tip body being proximate to a distal edge of the swaged portion of the electrode tip body.

15. The catheter system of claim 1, wherein the catheter body is formed from an electrically insulating and thermally insulating material.

16. An open-irrigated ablation catheter system, comprising:
   a catheter body;
   an electrode tip body mounted on a distal portion of the catheter body, the electrode tip body including a distal end and a swaged proximal end configured for connection to a distal end of the catheter body, the electrode tip body further including a central longitudinal axis and a wall defining an open interior region, the wall including one or more irrigation ports in fluid communication with the open interior region,
   wherein the wall is conductive for delivering radio frequency (RF) energy; and
   a proximal insert positioned partially within the catheter body and at least partially within the swaged proximal end of the electrode tip body,
   wherein the proximal insert includes a fluid inlet for receiving a cooling fluid delivered via the catheter body, and an exterior surface along an entire longitudinal length of the proximal insert, and
   wherein the exterior surface of the proximal insert includes annular ribs extending the entire longitudinal length of the proximal insert and forming channels between an interior surface of the proximal end of the electrode tip body and the exterior surface of the proximal insert, the channels being configured to direct the cooling fluid from the fluid inlet to cool the distal portion of the catheter body and to cool a junction of the catheter body and the electrode tip body, the channels being annularly disposed and extending the entire longitudinal length of the proximal insert.

17. The catheter system of claim 16, wherein all fluid flowing distally through the fluid inlet is directed through the channels between the interior surface of the proximal end of the electrode tip body and the exterior surface of the proximal insert.

18. The catheter system of claim 16, wherein the distal portion of the catheter body covers the swaged proximal end of the electrode tip body such that the junction of the catheter body and the electrode tip body is proximate to a distal edge of the swaged proximal end of the electrode tip body.

19. The catheter system of claim 16,
   wherein the proximal insert is includes a porous structure with open connected cells to promote heat exchange between the proximal insert and a cooling fluid at a junction of the catheter body and the electrode tip body the porous structure extending both proximally and distally relative to the junction of the catheter body and the electrode tip body.

20. The catheter system of claim 19, wherein the porous structure is a metal foam.

* * * * *